United States Patent [19]
Morris et al.

[11] Patent Number: 5,827,296
[45] Date of Patent: Oct. 27, 1998

[54] MEDICAL ELECTRICAL LEAD

[75] Inventors: Mary M. Morris, Mounds View; Peter M. J. Mulier, Stillwater, both of Minn.

[73] Assignee: Medtronic, Inc., Minneapolis, Minn.

[21] Appl. No.: 706,623

[22] Filed: Sep. 6, 1996

[51] Int. Cl.$^6$ ................................................. A61M 29/00
[52] U.S. Cl. ........................................ 606/129; 128/772
[58] Field of Search ................................. 607/132, 126, 607/122, 129; 128/772; 606/129; 604/160, 167

[56] References Cited

U.S. PATENT DOCUMENTS

| | | |
|---|---|---|
| 4,437,475 | 3/1984 | White . |
| 5,125,904 | 6/1992 | Lee . |
| 5,242,431 | 9/1993 | Kristiansen . |
| 5,250,033 | 10/1993 | Evans et al. . |
| 5,409,469 | 4/1995 | Schaerf . |
| 5,423,881 | 6/1995 | Breyen et al. . |
| 5,441,504 | 8/1995 | Pohndorf et al. . |

*Primary Examiner*—Scott Getzow
*Attorney, Agent, or Firm*—Michael J. Jaro; Harold Patton

[57] ABSTRACT

A medical electrical lead system featuring a medical electrical lead which features an improved anchoring sleeve. The medical electrical lead and anchoring sleeve cooperate with an introducer sheath to minimize the flow of blood through the introducer sheath during the introduction of the lead into the blood vessel. Specifically, the lead has a connector assembly, a conductor attached thereto and an electrode electrically coupled to the conductor. An insulative sleeve covers the conductor and an annular anchoring sleeve is movably positioned over the insulative sleeve. The anchoring sleeve has a distal end and a proximal end and further has an annular or circumferential seal within the inner lumen at the distal end. The distal end is further tapered along its exterior portion. The taper of the distal end cooperates with an introducer sheath to provide a seal between the outer portion of the anchoring sleeve and the introducer sheath. The circumferential seal on the same distal end cooperates with the medical electrical lead to create a seal between the anchoring sleeve and the medical electrical lead. In such a manner, a hemostatic seal is accomplished such that blood will not flow through the introducer sheath while the lead is within the introducer sheath and being positioned into the body.

12 Claims, 3 Drawing Sheets

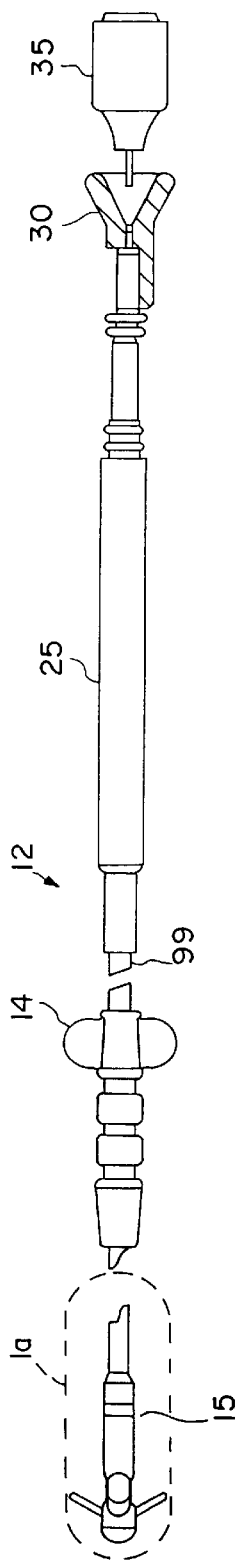
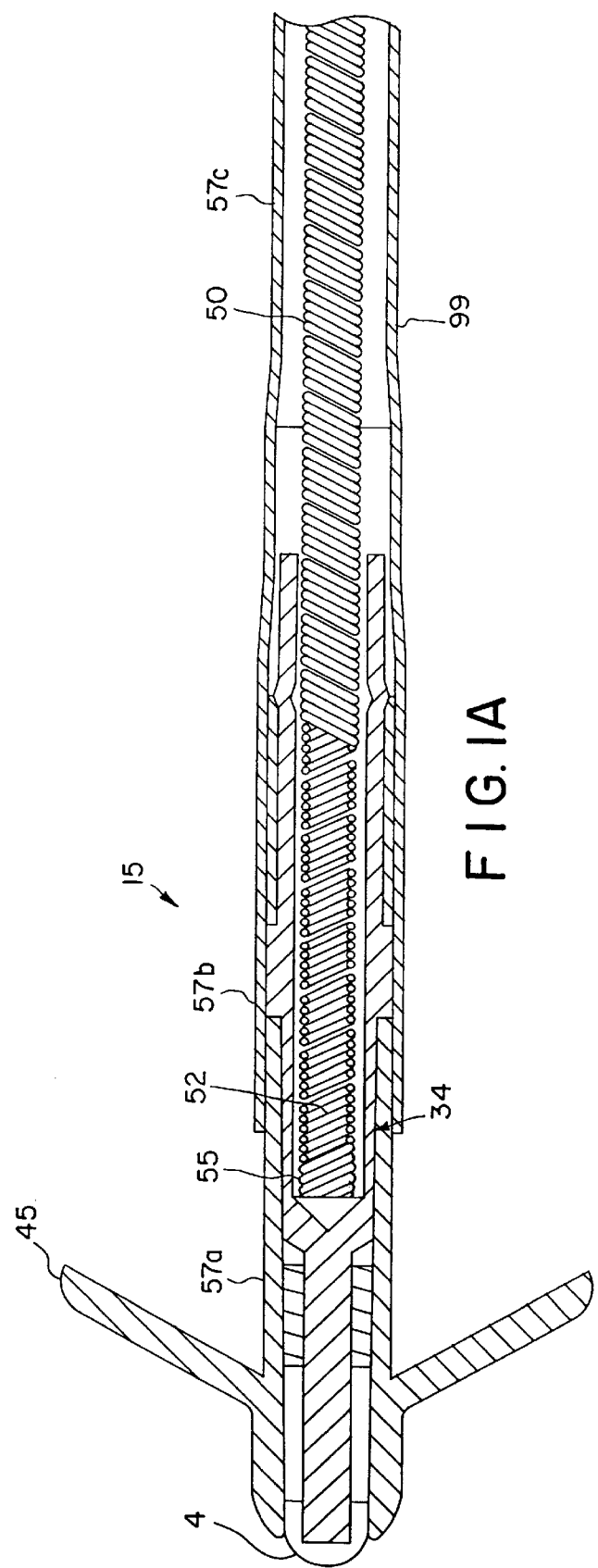
FIG. 1
FIG. 1A

MEDICAL ELECTRICAL LEAD

FIELD OF THE INVENTION

This invention relates to the field of body implantable medical electrical leads, and in particular, to a body implantable medical electrical lead which features an integrated anchoring sleeve to provide a hemostatic seal between the medical electrical lead and a lead introducer.

BACKGROUND OF THE INVENTION

In the medical field, various types of body-implantable medical electrical leads are known and used. One type of commonly used lead is an endocardial pacing lead.

Endocardial pacing leads are attached at their proximal end to an implantable pulse generator and at their distal end to the endocardium of a cardiac chamber. The distal end of an endocardial lead may engage the endocardium by either an active fixation mechanism or a passive fixation mechanism.

Active fixation mechanisms use a structure, such as a helix or hook, to physically engage into or actively affix themselves onto the heart. Passive fixation mechanisms, such as a tine assembly, lodge or passively fix themselves to the heart.

A preferred means for introducing an endocardial lead into the heart is through a vein. Through the implantation of a transvenous endocardial lead, the lead may be introduced into the heart using either the subclavian or cephalic vein in the shoulder area under the pectoral muscle.

To anchor the lead body at the venous entry site, the lead is secured to an anchoring sleeve, and the anchoring sleeve, in turn is secured to the surrounding tissue. Generally, the lead is secured to an anchoring sleeve using sutures, and the sleeve itself is thereafter secured to the tissue using sutures.

A multi-step procedure is often used to introduce such transvenous leads into the venous system. Generally, the procedure consists of inserting a hollow needle into a blood vessel, such as the subclavian. A guidewire is then passed through the needle into the lumen or interior portion of the blood vessel. The needle is then withdrawn and an introducer sheath and a dilator assembly is then inserted over the guidewire and into the lumen or interior portion of the blood vessel. This assembly is then advanced into a position suitable within the vessel, i.e., so that the distal end of the introducer and dilator assembly is well within the vessel, but the proximal end is outside the patient. Next, the dilator and guidewire are removed. The introducer sheath is left in this position and therefore offers direct access from outside the patient to the interior of the blood vessel. In such a fashion, a lead may then be passed into the vessel through the introducer sheath and ultimately be positioned within the heart.

One problem which may occur, however, with such a system, is that once the sheath has been inserted into the vein, blood may freely pass from the vein to the outside. In practice, a significant amount of bleeding may occur at the operation site, which requires constant mopping and cleaning. In addition, the open passage between the blood vessel to the outside provides an open passage for the introduction of air into the vein. The inadvertent introduction of air into the blood system may cause an air embolism, although highly unlikely, in the patient, and have a consequent negative effect. Previously, others have recognized this problem and offered solutions. U.S. Pat. No. 5,125,904 discloses a splittable hemostatic valve and sheath and a method for using the same. Such a system, however, is extremely cumbersome and expensive to produce. In addition, because of its complexity, it does not always operate in an acceptable manner. In addition, passage of the electrode on the distal end of a lead through such a valve may cause damage to the relatively delicate electrodes.

Thus, there is a need for a medical electrical lead which may cooperate with an introducer sheath to reduce the flow of blood through the introducer sheath.

SUMMARY OF THE INVENTION

It is thus an object of the invention to provide a medical electrical lead which functions with an introducer sheath to minimize the flow of blood through the introducer sheath during the introduction of the lead into the blood vessel. This and other objectives are met by the present invention which concerns a medical electrical lead system featuring a medical electrical lead having an improved anchoring sleeve designed to cooperate with an introducer sheath to minimize the flow of blood through the introducer sheath during the introduction of the lead into the blood vessel. Specifically, the lead has a connector assembly, a conductor attached thereto and an electrode electrically coupled to the conductor. An insulative sleeve covers the conductor and an annular anchoring sleeve is movably positioned over the insulative sleeve. The anchoring sleeve has a distal end and a proximal end and further has an annular or circumferential seal within the inner lumen at the distal end. The distal end is further tapered along its exterior portion. The taper of the distal end cooperates with an introducer sheath to provide a seal between the outer portion of the anchoring sleeve and the introducer sheath. The circumferential seal on the same distal end cooperates with the medical electrical lead to create a seal between the anchoring sleeve and the medical electrical lead. In such a manner, a hemostatic seal is accomplished such that blood will not flow through the introducer sheath while the lead is within the introducer sheath and being positioned into the body.

BRIEF DESCRIPTION OF THE DRAWINGS

FIG. 1 is a planned view of a medical electrical lead system.

FIG. 1a is a cross-sectional view of a lead assembly portion of the lead system of FIG. 1.

Figure 2:
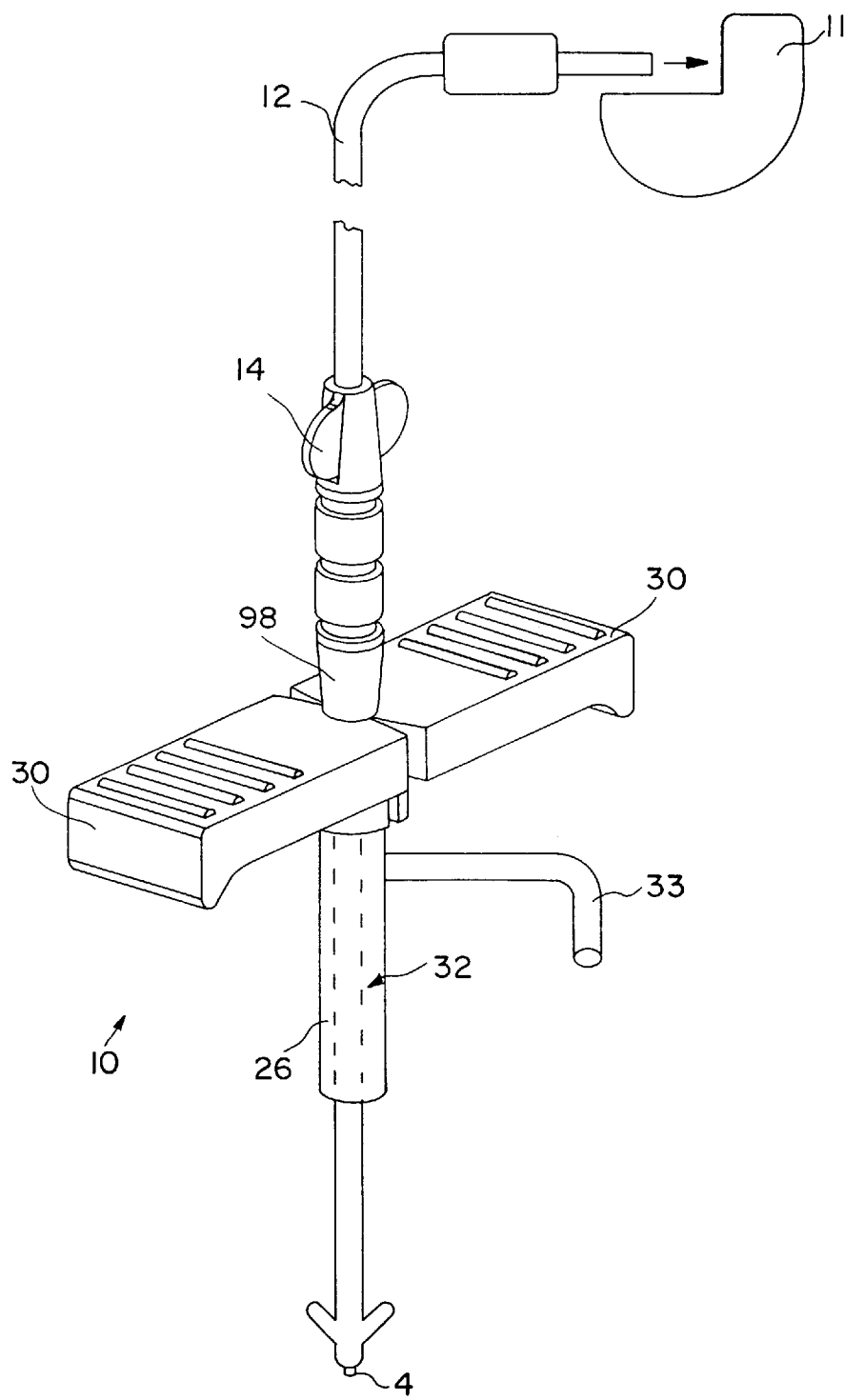
FIG. 2 is a detailed perspective view showing the lead disposed through an introducer sheath.

The drawings are not necessarily to scale.

DETAILED DESCRIPTION OF THE INVENTION

For the purposes of the specification and claims, the term "lead" is used herein in its broadest sense and includes pacing or defibrillation leads as well as any other types of stimulation leads, sensing leads, any combination thereof or any other elongated member, such as a catheter or tube, which may usefully be used within the body.

Referring now to the drawings, FIG. 1 shows a lead system 12 which includes a lead assembly 15, an anchoring sleeve 20, lead body 99, a connector pin 25, a stylet guide 30 and a stiffening stylet 35. As is well known in the art, once implanted stylet guide 30, and a stiffening stylet 35 are removed from lead.

Referring now to FIG. 1a, the lead assembly 15 is shown in greater detail with an electrode structure 4 at a distal end of the lead assembly 15, a tine 45 to secure the lead assembly 15 to the endocardium. Leads assembly 15, in turn is coupled to lead body 99. As seen, lead body 99 includes a lead conductor 50 in a multifilar coil configuration which allows the stiffening stylet 35 to be inserted into the lead assembly 15 in the internal lumen 52 of the lead conductor 50. The lead conductor 50 is shown attached at its distal end 55 to the electrode structure 4. The lead conductor 50 is also similarly attached at a proximal end (not shown) to the connector 25. In the preferred embodiment conductor 50 is a multifilar coil. Insulation elements 57a, 57b and 57c insulate portions of the electrode structure 4 and the lead conductor 50. Such insulation elements 57a, 57b, and 57c are preferably made from any suitable biocompatible polymer, such as silicone or polyurethane. The insulator 57c is typically a hollow polymeric tube extending between the proximal and distal ends of the lead assembly 15 and insulating the lead conductor 50 from surrounding body tissues. While a unipolar lead is shown, and described above, the present invention can also be applied to bipolar leads in the same manner. Moreover, the present invention is preferably used on any acceptable medical electrical lead, such as the Medtronic Model No. 5033 available from Medtronic Inc., Minneapolis, Minn.

Turning now to FIG. 2. As seen, lead 12, featuring anchoring sleeve 14 is disposed during introduction into a patient through introducer 10. As seen, introducer features a handle portion 30 and a sheath portion 26. Sheath portion and handle portion are integral or joined thereto and define a common lumen therethrough (best seen in FIG. 3.) Introducer is a typical introducer in its design to readily split or be slit lengthwise along a line 32 such that the introducer may be removed from the lead without going over an end of the lead. As seen, introducer may further feature a side port 33 which communicates with sheath 26. Side port 33 permits the introducer sheath to be flushed to thereby dissolve or remove any clots which may form.

Figure 3:
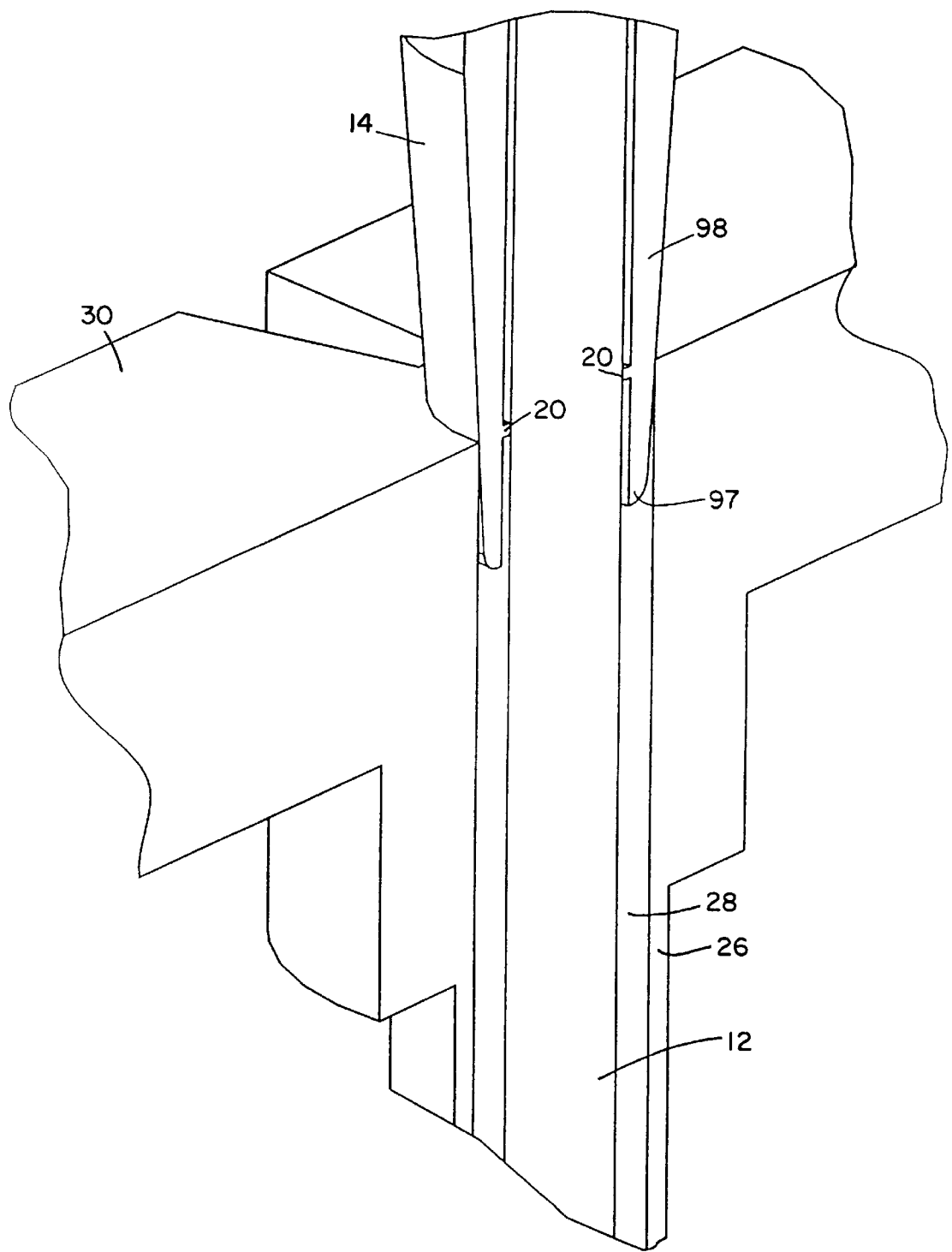
FIG. 3 is a detailed perspective view showing the interaction between the distal end of the anchoring sleeve and a standard introducer sheath which provides the hemostatic seal of the present invention.

Turning now to FIG. 3, as seen, the distal end 97 of anchoring sleeve 14 is dimensioned such that it cooperates with handle portion 30 of introducer 10. In particular, distal portion of anchoring sleeve 14 has a center lumen therethrough. Anchoring sleeve also has a taper on each end (best seen in FIG. 2). As seen, distal end 97 of anchoring sleeve tapers to a degree such that the distal end 97 of anchoring sleeve may be introduced through the lumen of handle portion 30. In addition, distal portion of anchoring sleeve 14 features an annular or circumferential seal 20 within inner lumen of anchoring sleeve 14. As seen, circumferential seal 20 is dimensioned such that it engages around and seals between the lead 12 and the sheath lumen 28.

Operation of the present invention is as follows. As discussed above, access to the vein is accomplished using a needle followed by a syringe which introduces a guidewire through the needle lumen into the blood vessel. Once the guidewire is in place, the needle is withdrawn and an introducer and dilator are inserted into the blood vessel. Following this, the guidewire is removed and the dilator is removed.

Next, the lead of the present invention inserted into the introducer and thereafter into the blood vessel. In particular, as discussed above, the anchoring sleeve 14 is inserted along with the lead into the introducer such that the distal-most end of anchoring sleeve is inserted into the sheath. In such a fashion, the distal end of anchoring sleeve and the seal 20 cooperate with the introducer sheath and the lead to seal against any blood from leaking from the vessel through the inner lumen of the sheath. This minimizes blood loss, thereby providing the physician with a clear view of the entry site and also prevents any air embolisms from forming.

Once the lead is satisfactorily positioned, the introducer 10 may be split as is conventional in the art (for example, by splitting the handle 30 and splitting the sheath 26 along the weakened line 32) so that the physician may peel the introducer away from the lead without having to remove the introducer from the end of a lead. Once the introducer is removed, the lead, and in particularly the anchoring sleeve, is anchored to the tissue and the lead body.

As a result of this construction, the physician, in fewer steps in less time, anchor the lead to the tissue adjacent the venous entry point while minimizing the flow of blood from the venous system and decreasing the risk of any air embolisms. In addition, the lead of the present invention permits simple prior art introducers to be used while still allowing for the minimization of blood loss. Overall, the lead of the present invention provides for a lead to be implanted into the patient using a standard introducer sheath which minimizes blood loss, is less likely to damage the lead, and reduces the risk of air embolism.

It is to be understood, that the present invention is not limited to use only in introducing atrial or ventricular pacing leads, and may be employed in introducing many of various types of therapeutic or diagnostic devices including transvenous leads intended to be disposed at various places within patient, as well as various other types of electrical leads, including nerve, muscle or defibrillation leads. It is to be further understood, moreover, the present invention may be employed in introducing many of various types of therapeutic or diagnostic catheters and is not limited only to the introduction of electrical leads. For purposes of illustration only, however, the present invention is below described in the context of the introduction of endocardial pacing leads. For the purposes of this specification and claims, the term "lead" is used herein in its broadest sense and includes a stimulation lead, a sensing lead, a combination thereof or any other elongated member, such as a catheter or guide wire, which may usefully be introduced into the body. Still other aspects, objects and advantages of the present invention can be obtained from the study of the specification, the drawings, and the appended claims. It will be understood various modifications and variations may be effective within the scope of the following claims. Such modifications may include substituting elements or components which perform substantially the same function in substantially the same way to achieve substantially the same result for those described herein.

What is claimed is:

1. A medical electrical lead system comprising an introducer assembly, the introducer assembly having a handle portion and a sheath portion, the sheath portion attached to the handle portion, the sheath portion having a lumen therethrough, the lumen having a lumen inner diameter, the introducer assembly having means for longitudinally separating the assembly into two corresponding parts;

a medical electrical lead disposed through the introducer assembly, the medical electrical lead having a connector pin, the connector pin coupled to a lead body, the lead body coupled to an electrode, the medical electrical lead further having an anchoring sleeve disposed over the lead body, the anchoring sleeve having a distal end and a proximal end, the distal end having a distal outer diameter, the anchoring sleeve lumen having an annular seal, the annular seal defines a reduced lumen within the sheath lumen, the reduced lumen having a reduced lumen diameter, the lead body having a lead body diameter, the reduced lumen diameter less than the lead body diameter;

characterized in that the distal outer diameter is less than the lumen inner diameter of the sheath portion of the introducer whereby when the distal end of the anchoring sleeve is inserted into the lumen of the sheath portion of the introducer assembly the flow of a fluid through the lumen is impeded.

2. A medical electrical lead system according to claim 1 wherein the distal end having a tapered end portion, the tapered end portion having a first tapered diameter greater than the lumen inner diameter and a second tapered diameter less than the lumen inner diameter, the second tapered diameter positioned distal relative to the first tapered diameter.

3. A medical electrical lead system according to claim 1 wherein the anchoring sleeve having an anchoring sleeve lumen threrethough, the lead body having a lead body diameter, the anchoring sleeve lumen greater than the lead body diameter.

4. A medical electrical lead system according to claim 3 wherein the annular seal positioned closer to the distal end of the anchoring sleeve than the proximal end of the anchoring sleeve.

5. A medical electrical lead system according to claim 4 wherein the annular seal is concentric about the anchoring sleeve lumen.

6. A medical electrical lead system according to claim 1 further comprising a flushing port couple to the sheath portion.

7. A method of inserting a medical electrical lead comprising the steps of:

providing an introducer assembly, the introducer assembly having a handle portion and a sheath portion, the sheath portion attached to the handle portion, the sheath portion having a lumen therethrough, the lumen having a lumen inner diameter, the introducer assembly having means for longitudinally separating the assembly into two corresponding parts;

inserting the sheath portion of the introducer assembly into the blood vessel;

providing a lead having an anchoring sleeve thereon, the anchoring sleeve disposed over the lead body, the anchoring sleeve having a distal end and a proximal end, the distal end having a distal outer diameter the distal end having a tapered end portion, the tapered end portion having a first tapered diameter greater than the lumen inner diameter and a second tapered diameter less than the lumen inner diameter, the second tapered diameter positioned distal relative to the first tapered diameter, the anchoring sleeve lumen having a annular seal, the annular seal positioned closer to the distal end of the anchoring sleeve than the proximal end of the anchoring sleeve, the annular seal defines a reduced lumen within the sheath lumen, the reduced lumen having a reduced lumen diameter, the lead body having a lead body diameter, the reduced lumen diameter less than the lead body diameter; and inserting the lead into the introducer such that the distal end is inserted into the sheath whereby when the distal end of the anchoring sleeve is inserted into the lumen of the sheath portion of the introducer assembly the flow of a fluid through the lumen is impeded.

8. A medical electrical lead system comprising:

an introducer having a sheath portion having a lumen therethrough, the lumen having a lumen inner diameter, the introducer having means for longitudinally separating the introducer;

a medical electrical lead disposed through the introducer, the medical electrical lead having an anchoring sleeve disposed over the lead body, the anchoring sleeve having a distal end and a proximal end, the distal end having a distal outer diameter, the distal outer diameter is less than the lumen inner diameter of the sheath portion of the introducer, the distal end having a tapered end portion, the tapered end portion having a first tapered diameter greater than the lumen inner diameter and a second tapered diameter less than the lumen inner diameter, the second tapered diameter positioned distal relative to the first tapered diameter, the anchoring sleeve having an anchoring sleeve lumen therethrough, the anchoring sleeve lumen having an annular seal, the annular seal defines a reduced lumen within the sheath lumen, the reduced lumen having a reduced lumen diameter, the lead body having a lead body diameter, the reduced lumen diameter less than the lead body diameter, the annular seal is dimensioned such that it engages around and seals between the lead and the sheath lumen, whereby when the distal end of the anchoring sleeve is inserted into the lumen of the sheath portion of the introducer assembly the flow of a fluid through the lumen is impeded.

9. A medical electrical lead system according to claim 8 further comprising the annular seal positioned closer to the distal end of the anchoring sleeve than the proximal end of the anchoring sleeve.

10. A medical electrical lead system according to claim 8 further comprising the lead body having a lead body diameter, the anchoring sleeve lumen greater than the lead body diameter.

11. A medical electrical lead system according to claim 10 wherein the annular seal is concentric about the anchoring sleeve lumen.

12. A medical electrical lead system comprising:

an introducer having a sheath portion having a lumen therethrough, the lumen having a lumen inner diameter, the introducer having means for longitudinally separating the introducer, the introducer having a flushing port couple to the sheath portion;

a medical electrical lead disposed through the introducer, the medical electrical lead having an anchoring sleeve disposed over the lead body, the anchoring sleeve having a distal end and a proximal end, the distal end having a distal outer diameter, the distal outer diameter is less than the lumen inner diameter of the sheath portion of the introducer, the distal end having a tapered end portion, the tapered end portion having a first tapered diameter greater than the lumen inner diameter and a second tapered diameter less than the lumen inner diameter, the second tapered diameter positioned distal relative to the first tapered diameter, the anchoring sleeve having an anchoring sleeve lumen threrethough, the anchoring sleeve lumen having an annular seal, wherein the annular seal is dimensioned such that it engages around and seals between the lead and the sheath lumen whereby when the distal end of the anchoring sleeve is inserted into the lumen of the sheath portion of the introducer assembly the flow of a fluid through the lumen is impeded.

* * * * *